United States Patent [19]
Winslow

[11] Patent Number: 5,922,774
[45] Date of Patent: *Jul. 13, 1999

[54] METHOD FOR CONTROLLING PLANT DAMAGE BY INSECT HERBIVORES

[75] Inventor: Anna Louise Winslow, Kennett Sq., Pa.

[73] Assignee: DCV, Inc., Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/734,914

[22] Filed: Oct. 22, 1996

[51] Int. Cl.$^6$ .......................... A01N 31/08; A01N 33/02; A01N 35/00; A01N 37/10
[52] U.S. Cl. .......................... 514/680; 514/569; 514/656; 514/657; 514/682; 514/732
[58] Field of Search ...................................... 514/680, 569, 514/682, 656, 657, 732

[56] References Cited

U.S. PATENT DOCUMENTS

| | | | |
|---|---|---|---|
| 3,663,253 | 5/1972 | Stone | 106/204 |
| 4,542,162 | 9/1985 | Rutherford et al. | 521/79 |

OTHER PUBLICATIONS

Trial et al., Emodin in Buckthorn: A Feeding Deterrent to Phytophagous Insects, *The Canadian Entomologist*, vol. III, pp. 207–212 (1979).

Reed et al, C.A. vol. 96 (1982) 96:16023C.

*Primary Examiner*—Allen J. Robinson

[57] ABSTRACT

Method for repelling insect herbivores from plant surfaces and deterring them from feeding on plant surfaces by applying an aqueous dispersion of polycyclic quinone or precursor thereof to the foliage of the plant and/or to the surrounding soil in which the plant is rooted.

10 Claims, 1 Drawing Sheet

METHOD FOR CONTROLLING PLANT DAMAGE BY INSECT HERBIVORES

FIELD OF INVENTION

The invention is directed to a method for controlling damage to plant life by insect herbivores. In particular, the invention is directed to such method which is safe environmentally.

BACKGROUND OF THE INVENTION

Agriculturists, such as farmers, orchard growers, gardeners, florists, and plant nursery operators, are all victims of the economic ravages which result from the consumption of plant foliage by various insect herbivores such as beetles and aphids. Heretofore, the principal method for controlling the damage from these sources has been the application of insecticides to the foliage. Insecticides are effective and economical in a superficial sense for the control of such pests in that they are economical for killing such pests. However, almost all of them have severe ecological disadvantages. For example, most of the pesticides used to control beetles are poisonous not only to humans, but also to wild animal life and birds as well as the pests they are intended to control. Furthermore, they are also poisonous to beneficial insects such as honeybees and butterflies, and predaceous insects such as ladybugs and the praying mantis. This latter effect has become so widespread that the honeybee population in the United States has been depleted by 20–25% in recent years. Such reduction in the population of honeybees, as well as other pollinating insects, has in many instances resulted in a substantial reduction in the agricultural yields of plants that depend on insect pollination, such as fruit trees, vegetables and floral species.

Though there are many organic farming methods which can reduce such ecological damage, those methods are frequently more expensive and less effective. For example, the planting of crops which beetles do not feed on in the vicinity of plants which are attacked by beetles and other herbivores can be limitedly effective. However, there remains a drastic need for economic means of controlling damage by insect herbivores, especially beetles, without simultaneously incurring risk either to humans, wild animal species, including birds, or to other insect species. In other words, there exists a long felt, widespread need for a method of controlling damage to crops by insect herbivores without incurring the risks of (1) poisoning the plants being treated, (2) poisoning the persons applying the treating material, (3) poisoning people who eat the treated plants, (4) poisoning animal species who come into contact with such treated plants and the materials for their treatment and (5) killing beneficial insect species on or in the vicinity of the treated plants.

SUMMARY OF THE INVENTION

In its broadest aspect, the invention is directed to a method of repelling insect herbivores from plant surfaces and also deterring them from feeding on plant surfaces. More particularly, the invention is directed to a method for repelling such insects and deterring their feeding on plants by applying an aqueous dispersion of polycyclic quinone or precursor thereof to the foliage of the plant and/or to the surrounding soil in which the plant is rooted.

The invention therefore includes a method for reducing the infestation of ground-metamorphosic insect herbivores on foliated plants comprising applying to the soil adjacent to the plant, prior to emergence of the adult stage from the soil, an aqueous dispersion of polycyclic quinone or precursor thereof.

The invention is also directed to a method for deterring insect herbivores from feeding on foliated plants comprising applying to the foliage an aqueous dispersion of polycyclic quinone or precursor thereof.

BRIEF DESCRIPTION OF THE DRAWING

The Drawing consists of FIGS. 1(a) through (e) in which various particulated forms of polycyclic quinone active material are depicted schematically 1.

DETAILED DESCRIPTION OF THE INVENTION

A. Polycyclic Quinones

Figure 1A:
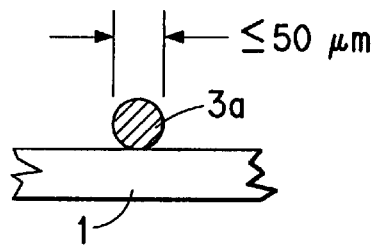
Figure 1B:
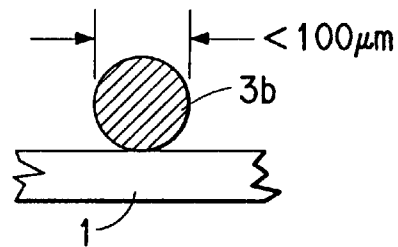
Figure 1C:
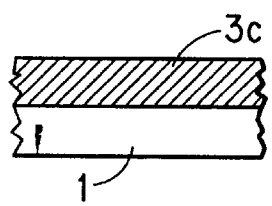
Figure 1D:
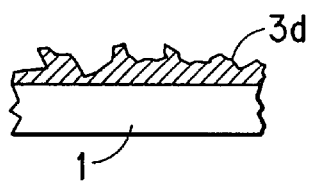
Figure 1E:
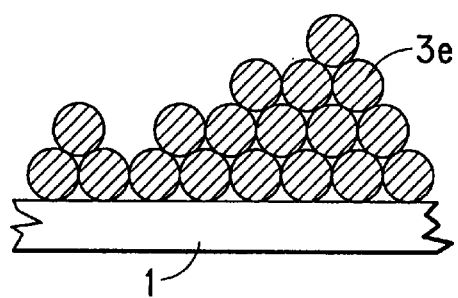

1. Composition:

A wide variety of polycyclic quinones can be used in the invention. As used herein, the term "polycyclic quinone" refers to bicyclic, tricyclic and tetracyclic condensed ring quinones and hydroquinones, as well as precursors thereof. On the whole, the non-ionic polycyclic quinones and polycyclic hydroquinones (herein referred to collectively as PCQs) have very low solubility in water at ambient temperatures. For use in the invention, it is preferred that such PCQs have a water solubility no higher than about 1,000 ppm, by weight.

However, as noted above, certain precursors of such PCQs can also be used in the invention either combined with the relatively insoluble PCQs or by themselves. Such precursors are anionic salts of PCQs which are water soluble under alkaline anaerobic conditions. However, these materials are not stable and are easily converted to the insoluble quinone form upon exposure to air. Thus, when anionic PCQs are applied to plants and exposed to air, they are quickly changed to the water-insoluble, more active quinone form.

Among the water-insoluble PCQs which can be used in the invention are anthraquinone, naphthoquinone, anthrone (9,10-dihydro-9-oxo-anthracene), 10-methylene-anthrone, phenanthrenequinone and the alkyl, alkoxy and amino derivatives of such quinones, 6,11-dioxo-1H-anthra[1,2-c]pyrazole, anthraquinone-1,2-naphthacridone, 7,12-dioxo-7,12-dihydroanthra[1,2-b]pyrazine, 1,2-benzanthraquinone, 2,7-dimethylanthraquinone, 2-methylanthraquinone, 3-methylanthraquinone, 2-aminoanthraquinone and 1-methoxyanthraquinone. Of the foregoing cyclic ketones, anthraquinone and methylanthraquinone are preferred because they appear to be more effective. Naturally occurring anthraquinones can be used as well as synthetic anthraquinones.

Other PCQs which can be used include insoluble anthraquinone compounds such as 1,8-dihydroxyanthraquinone, 1-amino-anthraquinone, 1-chloro-anthraquinone, 2-chloro-anthraquinone, 2-chloro-3-carboxyl-anthraquinone, 1-hydroxy-anthraquinone and unsubstituted anthraquinone. Various ionic derivatives of these materials can be prepared by catalytic reduction in aqueous alkali.

In addition, a wide variety of anthrahydroquinone compounds can be used in the method of the invention. As used herein, the term "anthrahydroquinone compound" refers to compounds comprising the basic tricyclic structure such as 9,10-dihydroanthrahydroquinone, 1,4-dihydroanthrahydroquinone, and 1,4,4a,9a-tetrahydroanthrahydroquinone. Anthrahydroquinone itself is 9,10-dihydroxyanthracene.

More particularly, both water-insoluble and water-soluble forms can be used. The non-ionic compounds are largely insoluble in aqueous systems, while ionic derivatives, such as di-alkali metal salts, are largely soluble in water. The water soluble forms are stable only in high pH anaerobic fluids. Low pH fluids (pH less than about 9–10) will result in the formation of the insoluble molecular anthrahydroquinone. Aerobic solutions will incur oxidation of the anthrahydroquinones to anthraquinone. Thus, anthrahydroquinones will not exist for long periods of time in an aerated environment such as that which is experienced by spraying. For these reasons, anthrahydroquinone treatments are usually implemented with the soluble ionic form in a caustic solution. Sodium hydroxide solutions are preferred over the hydroxides of other alkali metals for economic reasons.

2. Configuration:

It is known that the sensory organs of some insects are capable of more than one sensing function. For this reason it is not known with certainty whether the PCQs used in the invention are detected by the insect through its sense of taste or sight or smell. In fact, two or more senses may be involved. Nevertheless because of the very small size of the sensory organs of insects, it is preferred that the PCQ used be in physical form small enough to be touched by the sensory organs of the insect. That is, if the particles are too large, the taste sensors may pick up the taste poorly, if at all. Thus, for the PCQ to be more effective as a repellent, it is preferred to be of sufficiently small particle size that its taste can be sensed. Thus, the more effective quantity of repellent in any application is that which is in a form accessible to the insects' tongue; that is, it should be of sufficiently small size that it can be tasted.

Generally, because of these criteria, particles larger than about 50 micrometers cannot be adequately sensed and particles no larger than 30 micrometers are preferred. Similarly, smooth continuous surfaces of PCQ cannot be adequately sensed; and, of course, if the PCQ is coated with anything which is non-repellent to the insect or to which the insect is taste insensitive, the PCQ is ineffective. Though, strictly speaking, for the PCQ to be effective as a repellent it does not have to be in the form of discrete particles, nevertheless, the particles must be of sufficient size or have a contour that contains areas that are taste-accessible. This criterion is illustrated in the Drawing.

The particle in FIG. 1(*a*) would be accessible because it is sufficiently small. The particle in FIG. 1(*b*) would be less effective because it is too large to be sensed effectively. The smooth continuous coating in FIG. 1(*c*) would create little or no taste sensation because the large continuous surface would not have adequate access to the insects' taste sensors. On the other hand, the continuous coating shown in FIG. 1(*d*) would create at least moderate taste sensation because the protrusions are sufficiently small to be tasted. In this situation, the PCQ in the protrusions would be effective, but the PCQ in the main body of the coating would be less so, if at all. When the particles are portrayed as stacks of particles, as in FIG. 1(*e*), it can be seen that some of the particles in the upper layers would be accessible and therefore would be effective; but those particles in the lower layer would be less accessible and therefore less effective. The foregoing analysis shows clearly that the efficacy of the repellent is a function of both its configuration and accessibility. In turn, it can be seen that these variables are in large part dependent on the method of application.

When the PCQ is applied directly in particulate form, the size of the particles can be readily controlled. When such particles are applied as a single layer of particles, substantially all of the PCQ would be effective. However, if the particles are applied as a multiple of particle layers, essentially only the top layer would be effective. An important aspect of this analysis is that it is not important that the PCQ be applied as continuous covering. To the contrary, it is better that the coating of PCQ particles be discontinuous, at least on a micro scale, to enable functional exposure of the stomata of the foliage. Thus, the particles to be effective must be "particulated" in the sense that they contain areas which are accessible to the insects' taste apparatus.

3. Physical Properties—Volatility, Water Solubility:

It is important to the effectiveness of the invention that the PCQ, in whatever physical form it is applied, be persistent. That is, the applied active material must be able to resist erosion by wind and rain and other environmental forces to which the treated plant is exposed. For this reason, it is preferred (1) that the active form of the PCQ have a relatively low solubility in water so that it is not easily washed off the treated plant surfaces, and (2) that it have a relatively high melting temperature so that it does not undergo excessive evaporation from the treated plant surfaces during exposure to high ambient temperatures. For these reasons, it is preferred that the active PCQ material has a solubility in water under ambient temperature conditions of no more than about 1000 ppm and preferably in the range of 200–1000 ppm. The melting temperature of the active PCQ component should be at least about 150 C. and preferably at least 200 C.

Even when the active PCQ material possesses the above-described preferred physical properties, the material may have poor persistence because it does not adhere well to the plant surface to which it is applied. This is a function of the different surface properties of the foliage and the PCQ material. When this occurs, it is further preferred that the formulation contain a "sticking agent", i.e., a material which itself has good adhesion to the substrate and when mixed with the active material causes the PCQ to adhere to the substrate more firmly. Preferred sticking agents are aqueous polymer latices, which upon evaporation of the water therefrom, form a polymeric mass which is highly adhesive to the plant surface and holds particles of the active material firmly on the plant surface. Such latex sticking agents typically contain a small amount of surfactant dissolved in the aqueous phase.

A distinct advantage of the PCQ compounds which have been tested for use in the invention is that they are essentially non toxic, i.e., they have an $LD_{50}$ of at least 2,000 mg/kg in rats and preferably an $LD_{50}$ in rats of 5,000 mg/kg or higher. Because of this low toxicity of PCQs, they are not toxic to most insects or to birds, animals and humans. Moreover, the toxicity level is sufficiently low that any active material that becomes leached into the soil will not be detrimental to the normal constituents of fertile soil layers.

B. Coadjuvants:

As used herein, the term "coadjuvant" refers to materials which have a bio-activity different than the polycyclic quinones themselves. Such materials include fertilizers, fungicides, growth regulators, pesticides, herbicides and mixtures thereof. Both liquid and solid coadjuvants can be used in conjunction with the polycyclic quinones of the invention, depending on the manner of application. (See discussion below.) It should be noted, however, that the use of fungicides, pesticides and herbicides as adjuvants is not preferred because of the poisonous nature of such adjuvants. On the other hand, the use therewith of fertilizers and growth regulators does not appreciably reduce the benign nature of their admixtures with PCQs.

C. Additives:

As used herein, the term "additives" refers to materials which augment the effectiveness of the compositions of the invention, but which do not by themselves have bio-activity. These include such materials as surfactants, wetting agents, defoaming agents, extenders, sticking agents, penetrants, plasticizers, activators, spreading agents, diluents, odorants, brightening agents and the like.

D. Methods of Application:

A clear advantage of the invention is that it can be applied to growing plants in a number of different forms and methods of application. For example, the PCQ active material can be formulated in the form of powdery solids which can be applied by conventional spreaders, e.g., trough spreaders, such those used for planting grass seed, and by centrifugal (spinning disk) spreaders. Still in powder form, the PCQs can be sprayed as powders, either neat or in combination with solid powder extenders and/or various coadjuvants.

Likewise, when the PCQs are in powder form, they can be dispersed in a liquid media, especially water, and sprayed as a liquid suspension. On the other hand, when water-soluble precursors of the PCQs are used, they can be dissolved in water for dilution and then applied by spraying in the usual manner. The aeration, which occurs during spraying is sufficient to convert the soluble salt to the more active water-insoluble form. In both of these techniques either solid or liquid coadjuvants can be used. For example, water-soluble coadjuvants can be dissolved in the liquid medium or water-insoluble coadjuvant particles can be suspended in the liquid medium along with the PCQ and/or PCQ precursor.

In general, quite dilute applications of the PCQs to plant surfaces or to the ground are effective to deter insect damage. For example, the application of liquid dispersions containing as little as 100 ppm by weight PCQs can be effective to reduce insect damage to many plants. At least 500 ppm is preferred. Similarly, the application of liquid dispersions to the ground can be effective to deter emerging pests when the ground is covered with as little as 50 mg/m$^2$ of active PCQ. It will be recognized, however, that the effective dose level of the active component varies widely, both with the type of insect infestation which is being treated and the composition of the active component. Fortunately, higher concentrations of PCQs can be tolerated with complete safety both to the environment and to humans and other animals.

It will be recognized from the foregoing discussion, that not all of the PCQ coatings may be of suitable configuration for tasting. However, so long as a sufficient fraction of the coating is available to the insects' taste organs, the composition will effectively deter the insects from feeding on the foliage.

It has been observed that not all of an area from which it is desired to deter insect infestation needs to be treated. For example, untreated areas adjoining treated areas are frequently free of similar insects because of their proximity to treated areas. Furthermore, complete coverage of the foliage with active material is not necessary since the proximity of the untreated foliage parts to the treated parts is often sufficient to bring about substantial deterrence. As noted above, it is preferred that the plant leaves not be continuously coated in order that the stomata are not covered and will, therefore, be fully functional. Nevertheless, it will ordinarily be necessary to spray new plant growth to avoid reinfestation by whatever insect is being pursued.

It will be recognized by those skilled in the formulation of agricultural chemicals that other dispersion media than water can be used. For example, safe, degradable oils, such as vegetable oils, can be used. However, from the standpoint of safety and environmental health, it is much preferred to use water.

E. Plants to be Treated

None of the plants which are subject to damage by insects are in any way harmed by the application of aqueous dispersions of PCQs; nor has there been observed any detrimental effect on either the growth or overall health of untreated plants located near such treated plants. As noted above, it is believed that care should be taken not to cover the treated plant surfaces so heavily as to block stomata activity. Otherwise, even concentrated dispersions have no adverse effect on the treated plants.

Though, most of the testing work carried out to date has been conducted on garden vegetables and flowers, the method is similarly effective on insect pests afflicting fruit trees. Among the fruit tree pests which can effectively be treated by the method of the invention are plum curculios, codling moths, tarnished plant bugs, aphids, mealy aphids, red spider moths, fall webworms and green fruit worms. The invention is most effective on fruit trees when it is used at the pink tip stage and thereafter in a normal spraying schedule ending shortly before harvest. As used herein, the term "pink tip stage" refers to the stage of tree growth when the fruiting bud has formed and color becomes apparent.

F. Pests Which Are Repelled

The invention appears to be effective against virtually all ground-metamorphosic insect herbivores in the adult stages and many insects in their larval stage. Thus, the invention can be used to deter growing plant damage by coleoptera (beetles) such as Japanese beetles, Mexican bean beetles and squash vine borers, as well as homoptera, such as aphids, and hemiptera (bugs), such as the chinch bug, squash bug, stink bug, tarnished plant bug, flower bug and lace bug. Also, the PCQs do reduce the presence of diptera, such as saw flies, who lay their eggs in the stems of growing plants. However, the PCQs used in the invention clearly do not interfere with the unharmful activities on treated plants of members of non-herbivorous orders, such as hymenoptera (ants, bees and wasps) and lepidoptera (butterflies and moths). Use of the invention is also harmless to lady bugs, the praying mantis, dragonflies and other predaceous insects.

EXAMPLES

The following described tests and observations were made during the growing season of a conventional flower and vegetable garden located in Plant Hardiness Zone 7. Unless otherwise stated, the treating material was an aqueous dispersion containing 10% by weight finely divided particles of 9,10-anthraquinone and a small amount of organic surfactant. The average particle size of the anthraquinone was approximately 25 micrometers. This polycyclic quinone component is referred to in the following examples as AQ.

Example 1

An infestation of Japanese beetles (popillia Japonica) was observed on the leaves of a Canna plant (Canna x. generalis). Upon spraying the leaves with the above-noted aqueous dispersion of AQ, the Japanese beetles departed and no further beetle damage was observed. The following day, two Japanese beetles were placed in a glass jar with an untreated Canna leaf and a treated Canna leaf. One of the beetles was marked for identification, sprayed with the AQ dispersion and both beetles were observed for three days. Both of the beetles lived. There was no further damage to the treated leaf; but the untreated leaf exhibited further damage.

Example 2

The leaves, but not the flowers, of a Canna plant were sprayed with AQ dispersion. The plant was and continued to be free of Japanese beetle infestation. The beetles avoided the plant entirely, including the untreated flowers. However, bees, butterflies and hummingbirds continued to alight on the flowers and otherwise continued normal activity around the plant. Interestingly, it was observed that there no beetle activity on neighboring dahlia plants, which had not undergone treatment with AQ dispersion.

Example 3

An untreated Canna plant was observed to have substantial leaf damage and a substantial infestation of Japanese beetles. The damaged leaves as well as the flowers were sprayed with AQ dispersion, after which there was no further damage to either the treated leaves or the treated flower surfaces. Shortly after the application of AQ dispersion, there was a substantial rain and new leaf growth appeared. Japanese beetles attacked the new growth, but there was no further damage to the treated leaves or to the flowers. Upon treating the new growth, no further beetle damage occurred.

Example 4

Japanese beetle damage was observed on the bush and flowers of five rose bushes. Both the leaves and flowers of the affected rose plants were sprayed with the above-described aqueous AQ dispersion, which halted all further beetle damage. The plant was also free of aphids. A few days later, Japanese beetles reinfested the plant on the new growth of the leaves, buds and flowers. The new growth was then sprayed and no further damage was observed on the treated areas. It was also noted that there was no diminution in butterfly, wasp and honeybee activity around the plant.

Example 5

The leaves of a mature hollyhock plant having extensive beetle damage were sprayed with AQ dispersion, after which there was no further damage from the beetles.

Example 6

Three pairs of Canna plants, which had been previously treated with AQ dispersion to halt Japanese beetle damage, experienced further beetle damage on new plant growth. The new growth of all six plants was carefully sprayed with AQ dispersion to avoid hitting the beetles on the new growth. Tobacco cloth was then suspended over one of each pair of plants in such manner that it shaded, but did not touch, the plants or the ground surrounding the plants. Upon observing the plants for two days, no beetles remained and there was no further damage to any of the six plants, whether they had been shaded or not.

Example 7

In this second growing season during which the effect of AQ treatment has been observed, it was noted that overall beetle infestation was lower than the previous year. For example, there was no beetle infestation on red raspberry plants, which are usually favorite targets of Japanese beetles. This effect appears to be the result of the presence, on or near the surface of the ground adjacent to previously treated plants, of residual amounts of AQ from previous sprayings. Because of (1) the chemical stability of AQ and (2) its low water solubility, this observation indicates that the residual AQ on or near the surface of the ground had an interfering effect on the emergence of beetle pupa from the ground. A similar reduction in aphid infestations was observed on rose bushes.

Example 8

It was observed that several squash vines contained an infestation of squash bugs (*Anasa tristis*). Using 0.5% wt. AQ dispersion, the squash vine leaves, stems, and adjacent soil were sprayed. No bugs were killed and, within five minutes, all infestation had left. Two days later, it was noted, quite unexpectedly, that squash bugs returned to the treated vines. Though the bugs seemed to be very active on their return, they were not observed to inflict any damage to the vine surfaces.

Throughout the above tests on the use of aqueous AQ suspension to reduce damage to plants from herbivorous insects, it was observed that none of the insects on the plants, whether harmful or not, was killed. They were repelled in most cases and deterred from eating, but because of the negligible toxicity of the PCQ component, none were killed.

Example 9

The hanging fruit of a dwarf five-in-one pear tree was damaged by birds, after which the damaged fruit was beset by wasps, yellow jackets, flies and gnats. At the same time, fallen fruit beneath the tree was being consumed by crows, butterflies, honeybees, yellow jackets and flies. The foliage and hanging fruit on the tree were sprayed generally with aqueous AQ dispersion; but the ground beneath the tree containing fallen fruit was not sprayed. The spraying of each individual pear on the tree was not attempted. Upon completion of the foliage spraying, the tree held both damaged and undamaged fruit. Soon after this spray treatment, all insect activity on the hanging fruit ceased. However, several hours later, yellow jacket activity resumed on the bird-damaged hanging fruit. There was no harmful insect or bird activity on either the undamaged hanging fruit or the foliage. Both insect activity and bird activity on the fallen fruit lying on the untreated ground beneath the tree continued unabated. No insect activity on the sprayed portions of the tree was observed through the picking season.

Examples 10–16

A series of tests was run in which various garden insects were placed in vented glass jars with plant leaves, some of which had been treated and some not treated, as indicated. As used herein, the term "treated" indicates that the referred-to surface had been treated with the aqueous AQ dispersion:

Example 10

A grasshopper was placed in a jar with treated rose and dahlia leaves. After three days, there was no sign of leaf damage by the grasshopper. The grasshopper still lived and was released;

Example 11

A grasshopper was placed in a jar with treated dahlia leaves. During two days in the jar, the grasshopper deposited several eggs; but there was no damage to the treated leaves;

Example 12

Fall webworms were placed in a jar with treated dahlia and pear tree leaves. At the end of three days, the dahlia leaves were untouched, but the pear leaves showed damage from the webworms;

Example 13

A small fruit fly was placed in a jar with a heavily treated squash vine leaf. After four days, the fly was still alive, but there was no damage to the leaf;

Example 14

A scorpion fly (Mecoptera) was placed in a jar with treated and untreated rose leaves. The fly fed on the untreated leaf, but avoided the treated leaf entirely;

Example 15

A Japanese beetle was removed from a rose bush and placed in a jar with treated rose leaves only. Having no alternative, the Japanese beetle fed on the treated leaves; and Example 16

A Mexican bean beetle was kept in a jar for five days with lightly coated bean plant leaves. Similarly to the observed actions of the Japanese beetle described in Example 15, the beetle fed on the lightly treated leaves throughout that time.

Example 17

In separate experiments, one area of ground was sprayed with a U-shaped barrier of AQ dispersion and a second area was sprayed with an enclosed circle of AQ dispersion. Several ants were placed within the two enclosures. In the former case, the ants quickly left through the open end of the U-shaped enclosure. In the latter case, the ants milled around for several minutes apparently looking for a way out. The ants then followed a leading ant over the sprayed line.

What is claimed is:

1. An environmentally safe method for reducing infestation of ground-metamorphosic insect herbivores on foliated plants, without inhibiting the action of insects which are predaceous to such herbivores, comprising applying to the ground surface adjacent to the plant, prior to emergence of the adult stage of the insect herbivore, solid particles of anthraquinone or anthrahydroquinone, which particles are accessible to the taste of the insect herbivores, in such amount that the concentration thereof on the ground is at least 50 mg/M$^2$, the average size of the particles being no greater than 100 micrometers and the particles are applied in the form of an aqueous dispersion of (1) water-insoluble non-ionic particles suspended in the aqueous medium, or (2) a solution of the ionic salt of such compounds, which salt is converted to the water-insoluble non-ionic form upon exposure to air following such application, the particles being further characterized as hving a solubility in water of less than 1,000 ppm by weight, a melting point of at least 150 C., and an LD$_{50}$ of at least 2,000 mg/kg in rats.

2. An environmentally safe method for reducing infestation of ground-metamorphosic insect herbivores on foliated plants, without inhibiting the action of insects which are predaceous to such herbivores, comprising applying to the foliage solid particles of anthraquinone or anthrahydroquinone, which particles are accessible to the taste of the insect herbivores, in such amount that the concentration of particles in the dispersion is at least 100 ppm by weight, the average size of the particles being no greater than 100 micrometers and the particles are applied in the form of an aqueous dispersion of (1) water-insoluble non-ionic particles suspended in the aqueous medium or (2) a solution of the ionic salt of such compounds, which salt is converted to the water-insoluble non-ionic form upon exposure to air following such application, the particles being further characterized as having a solubility in water of less than 1,000 ppm by weight, a melting point of at least 150 C., and an LD$_{50}$ of at least 2,000 mg/kg, in rats.

3. The method of claim 2 in which the application is repeated on new growth of the plant.

4. The method of claim 2 in which the foliated plant is flowering and the dispersion is applied only to the foliage and not to the opened flower surfaces.

5. The method of claim 2 in which the foliated plant is flowering and the dispersion is applied prior to budding and opening of the flowers.

6. The method of claim 2 in which the foliated plant is flowering and the dispersion is applied to the opened flower surfaces.

7. The method of claim 2 in which the insect herbivore is in the larval stage.

8. The method of claim 2 in which the insect herbivore is in the adult stage.

9. The method of claim 2 in which the dispersion is applied to the foliage of fruit trees at the pink tip stage.

10. The method of claim 2 in which the application of the dispersion is repeated plurally prior to harvest.

* * * * *